United States Patent
Schneider et al.

(10) Patent No.: US 9,068,962 B2
(45) Date of Patent: Jun. 30, 2015

(54) METHOD AND APPARATUS FOR DETERMINING ASPHALTENE YIELD AND FLOCCULATION POINT OF CRUDE OIL

(71) Applicant: Schlumberger Technology Corporation, Sugar Land, TX (US)

(72) Inventors: Marc Schneider, Walheim (DE); Abdel M. Kharrat, Edmonton (CA); Farshid Mostowfi, Edmonton (CA); Vincent Sieben, Edmonton (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/348,611

(22) PCT Filed: Mar. 1, 2013

(86) PCT No.: PCT/US2013/028514
§ 371 (c)(1),
(2) Date: Mar. 30, 2014

(87) PCT Pub. No.: WO2013/130930
PCT Pub. Date: Sep. 6, 2013

(65) Prior Publication Data
US 2014/0375991 A1 Dec. 25, 2014

Related U.S. Application Data

(60) Provisional application No. 61/605,524, filed on Mar. 1, 2012.

(51) Int. Cl.
| | |
|---|---|
| *G01N 33/28* | (2006.01) |
| *G01N 31/16* | (2006.01) |
| *G01N 21/83* | (2006.01) |
| *G01N 21/25* | (2006.01) |

(52) U.S. Cl.
CPC ........ *G01N 33/28* (2013.01); *G01N 31/16* (2013.01); *G01N 21/83* (2013.01); *G01N 33/2823* (2013.01); *G01N 21/25* (2013.01)

(58) Field of Classification Search
CPC ........ C07C 55/10; C07C 51/02; C07C 51/43; C07C 51/412; C07C 51/445; C07C 51/44; C07C 29/149; C07C 51/46; C07C 31/207; C07C 55/14; C07C 51/235; C07C 2/58; C07C 55/02; C07C 57/13; C07C 57/15
See application file for complete search history.

(56) References Cited

U.S. PATENT DOCUMENTS

| | | |
|---|---|---|
| 8,269,961 B2 | 9/2012 | Mostowfi et al. |
| 2010/0136698 A1 | 6/2010 | Dadic et al. |
| 2011/0292382 A1* | 12/2011 | Mostowfi et al. ............. 356/246 |

FOREIGN PATENT DOCUMENTS

| | | |
|---|---|---|
| EP | 1813348 | 8/2007 |
| WO | 2011/151746 | 12/2011 |
| WO | 2013/126732 | 8/2013 |

OTHER PUBLICATIONS

Bowden, Stephen A., et al. "Determination of the asphaltane and carboxylic acid content of a heavy oil using a microfluidic device," Lab on a chip, 2009, vol. 9, No. 6, pp. 828-832.

*Primary Examiner* — Michael P Stafira
(74) *Attorney, Agent, or Firm* — Robert A. Van Someren; Wayne I. Kanak

(57) ABSTRACT

A method for determining an asphaltene yield curve and an asphaltene flocculation point includes obtaining a crude oil sample and measuring an optical spectrum of the crude oil sample. A titrant is then mixed with the crude oil sample at different concentrations. At each concentration, precipitated asphaltenes are filtered from the mixture and the optical spectrum of the filtrate is measured. The optical spectrum of the filtrate is then subtracted from the optical spectrum of the crude oil sample. A fractional asphaltene precipitation is determined for each concentration of titrant. A flocculation point is determined corresponding to an inflection point in the fractional asphaltene precipitation for each concentration of titrant.

24 Claims, 12 Drawing Sheets

METHOD AND APPARATUS FOR DETERMINING ASPHALTENE YIELD AND FLOCCULATION POINT OF CRUDE OIL

BACKGROUND

The measurement of asphaltene content of a hydrocarbon reservoir fluid is a common aspect of oil production, transportation, and refining. Because asphaltenes are not generally well defined and not well understood, numerous methods have been developed for characterizing and quantifying asphaltenes in such reservoir fluids. Conventional methods, however, require large quantities of sample reservoir fluids and solvents, large glass vessels, and many other instruments for proper extraction of the asphaltenes. Typically, the quantification of asphaltenes is performed by weighing asphaltenes extracted from the reservoir fluid, generally must be performed in a laboratory environment, and requires significant lengths of time to complete.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, a method for determining an asphaltene yield curve and an asphaltene flocculation point is provided. The method includes obtaining a crude oil sample, measuring an optical spectrum of the crude oil sample, setting a minimum titrant concentration; mixing the crude oil sample with a titrant to produce a crude oil-titrant mixture, and filtering precipitated asphaltenes from the crude oil-titrant mixture to produce a filtrate. The method further includes measuring an optical spectrum of the filtrate and subtracting the optical spectrum of the filtrate from the optical spectrum of the crude oil sample. The titrant concentration is increased and the steps of mixing the crude oil sample with the titrant, filtering the precipitated asphaltenes, measuring the optical spectrum of the filtrate, and subtracting the optical spectrum of the filtrate from the optical spectrum of the crude oil sample are repeated until the entire asphaltene yield curve is established. The method further includes determining a fractional asphaltene precipitation for each concentration of titrant and determining a flocculation point corresponding to an inflection point in the fractional asphaltene precipitation for each concentration of titrant.

In another aspect, a system for determining an asphaltene yield curve and an asphaltene flocculation point is provided. The system includes a first mixer in fluid communication with a crude oil source and a titrant source, a microfluidic reactor in fluid communication with the mixer, and a filter in fluid communication with the microfluidic reactor. The system further includes a second mixer in fluid communication with the filter and in fluid communication with a first solvent source and an optical cell operably associated with the second mixer.

In yet another aspect a system for determining an asphaltene yield curve and an asphaltene flocculation point is provided. The system includes a microfluidic chip, a mixer operably associated with the microfluidic chip, a first solvent pump in fluid communication with the mixer, and an optical cell. The microfluidic chip includes a crude oil sample inlet port, a titrant port, and a mixer and reactor section in fluid communication with the crude oil sample inlet port and the titrant port. The microfluidic chip further includes a filter in fluid communication with the mixer and reactor section, the filter having an inlet side and an outlet side; a waste port in fluid communication with the inlet side of the filter; and a product port in fluid communication with the outlet side of the filter. The optical cell is in fluid communication with the product port.

BRIEF DESCRIPTION OF THE DRAWINGS

Embodiments of the disclosed subject matter of the application are described with reference to the following figures. The same numbers are used throughout the figures to reference like features and components.

Figure 1:
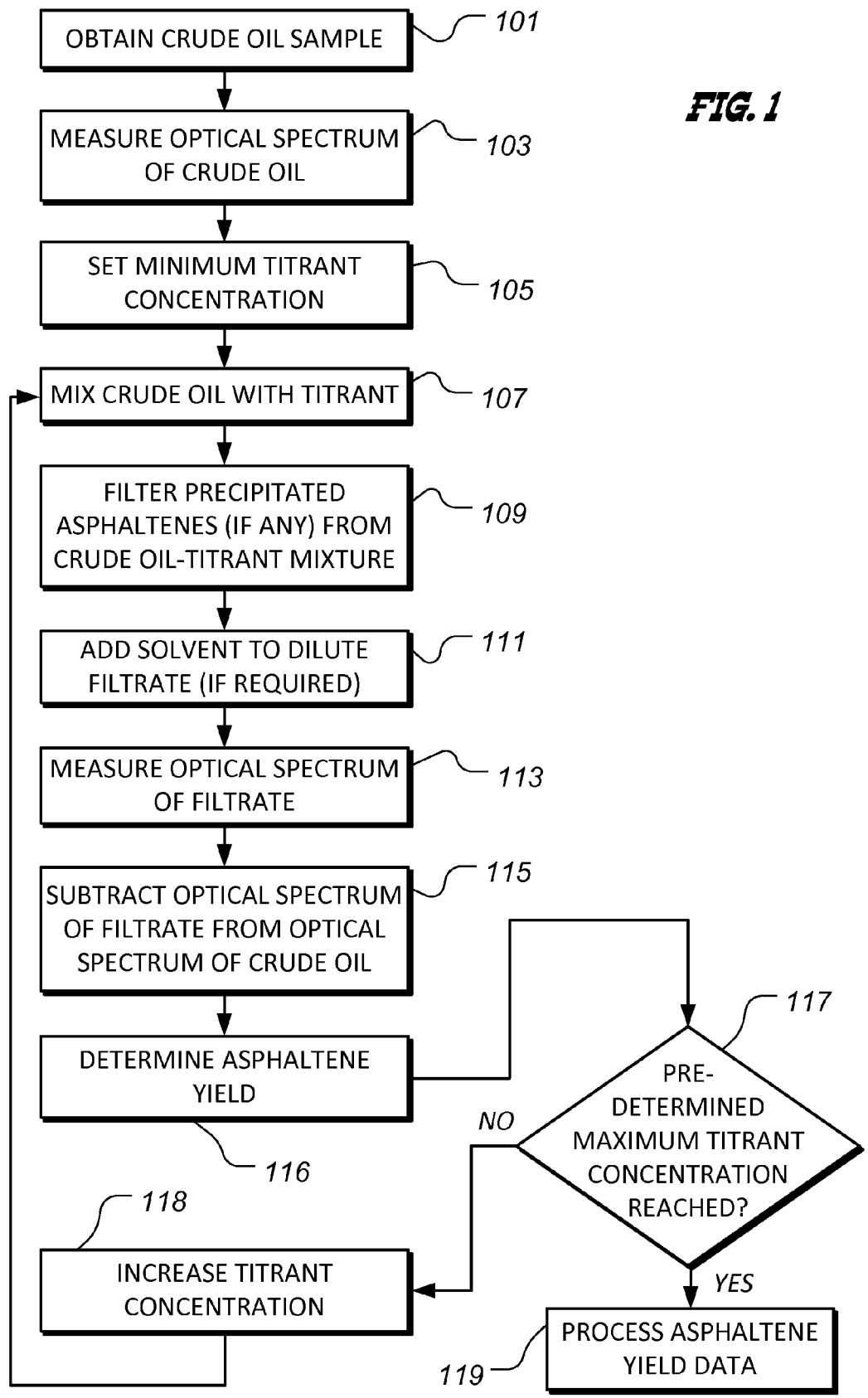
FIG. 1 is a flow chart of an illustrated embodiment of a method for generating data for an asphaltene yield curve and an asphaltene flocculation point for a crude oil sample.

While the disclosed subject matter is susceptible to various modifications and alternative forms, specific embodiments thereof have been shown by way of example in the drawings and are herein described in detail. It should be understood, however, that the description herein of specific embodiments is not intended to limit the disclosed subject matter of the application to the particular forms disclosed, but on the contrary, the intention is to cover all modifications, equivalents, and alternatives falling within the scope of the disclosed subject matter as defined by the appended claims.

DETAILED DESCRIPTION

Illustrative embodiments of the disclosed subject matter of the application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

The disclosed subject matter of the application relates to a method and an apparatus for determining the asphaltene yield and the asphaltene flocculation point for a crude oil sample.

Generally, asphaltenes are the heaviest and most polar components in crude oil. The asphaltene fraction of a crude oil sample is generally defined as the fraction that is insoluble in an alkane, such as, for example, n-heptane or n-pentane, but soluble in an aromatic hydrocarbon, such as toluene. The deasphalted fraction of crude oil is commonly referred to as the maltene fraction. Asphaltenes typically exhibit significant optical absorbance or optical density in the visible light spectrum, while maltenes exhibit less optical absorbance or optical density in the visible light spectrum than asphaltenes. Considering crude oil as a combination of asphaltenes and maltenes, with the asphaltene fraction and the maltenes fraction of a crude oil sample each exhibiting a particular optical density or coloration, the linear addition of the optical density of each fraction results in the optical density or coloration of the crude oil sample. Comparison and calculation of the optical densities of crude oils and the crude oil fractions, that is, the asphaltenes and maltenes, is performed at substantially equal concentrations. Therefore, if a fraction, such as an asphaltene fraction or a maltenes fraction, is extracted from a crude oil sample, the extracted volume is replaced by a transparent solvent.

Typically, the asphaltene content of a crude oil sample is measured at a ratio of about one part crude oil to 40 parts alkane. At such concentrations of n-alkane, asphaltene precipitation is generally at a maximum. As the ratio of alkane to crude oil is reduced, the amount of asphaltene precipitation also is typically reduced. By varying the ratio of crude oil to alkane, that is, using the alkane as a titrant, an asphaltene yield curve can be generated, which graphically describes the amount of precipitated asphaltenes as a function of alkane concentration. Such asphaltene yield curves reveal valuable information about solubility and the phase separation of asphaltenes, including determining the asphaltene flocculation point of a crude oil sample. The asphaltene flocculation point is revealed as an inflection point in the asphaltene yield curve, indicating the alkane concentration at which the first particles of asphaltenes precipitate.

FIG. 1 provides a flow chart representing an illustrative embodiment of a method for determining the asphaltene precipitation from a crude oil sample based upon the concentration of titrant or alkane. This data can be used to determine an asphaltene yield curve and an asphaltene flocculation point of a crude oil sample. In the illustrated embodiment, a crude oil sample is obtained (block 101). It should be noted that the obtained sample may be a sample that is retrieved and transported to another location, such as a laboratory, for analysis, or a sample that is retrieved and analyzed in the field. The scope of the disclosed subject matter of the application is not limited by the means by which the crude oil sample is obtained. Returning to FIG. 1, the optical spectrum of the crude oil sample is measured (block 103). It should be noted that the crude oil sample may include a solvent if the optical spectrum of the crude oil sample alone is outside the measureable range of the equipment being used to determine the optical spectrum of the crude oil. A minimum titrant concentration is set (block 105), which is insufficient to produce asphaltene precipitation. In one embodiment, the titrant is an alkane, such as n-heptane. However, in other embodiments, the titrant may be another alkane, such as n-pentane or the like, or another material. The crude oil is then mixed with the titrant (block 107). Although no asphaltenes will precipitate initially, as the titrant concentration is gradually increased in steps, at some titrant concentration at least some asphaltenes will precipitate from the crude oil. In any case, the crude oil-titrant mixture is filtered (block 109), if required a solvent is added to dilute the filtrate (block 111), and the optical spectrum of the filtrate is measured and subtracted from the optical spectrum of the crude oil (blocks 113 and 115). Thereafter, the asphaltene yield is determined (block 116) and a determination is made as to whether or not a predetermined maximum titrant concentration has been reached (block 117). As this will not initially be the case, the titrant concentration is increased (block 118) and the new, higher titrant concentration is mixed with a fresh sample of the crude oil (block 107) to ultimately precipitate at least some asphaltenes from the crude oil. The precipitated asphaltenes are then filtered from the crude oil-titrant mixture (block 109). The portion of the crude oil remaining after the precipitated asphaltenes are removed, that is, the filtrate, comprises maltenes and, in some situations, asphaltenes, if all asphaltenes have been not precipitated from the crude oil. Maltenes are species having lower molecular weights than asphaltenes and are soluble in the titrant. If the optical density of the filtrate is outside the measurable range of the equipment being used to determine the filtrate's optical spectrum, a solvent is added to the filtrate (block 111). Next, the optical spectrum of the filtrate is measured (block 113) and subtracted from the optical spectrum of the crude oil prior to any asphaltenes being removed (block 115). The resulting optical spectrum corresponds to the optical spectrum of the asphaltenes precipitated from the sample of crude oil at a specific concentration of titrant. The asphaltene yield is then determined at the specific titrant concentration (block 116) and a determination is made as to whether or not the predetermined maximum titrant concentration has been reached (block 117). If the predetermined maximum titrant concentration has not been reached, the concentration of titrant is increased (block 118) and the process returns to block 107. This cycle is carried out until the asphaltene yield curve, a dataset representing asphaltene precipitated from the crude oil at different titrant concentrations, is established to the extent defined by the predetermined maximum titrant concentration.

Figure 2:
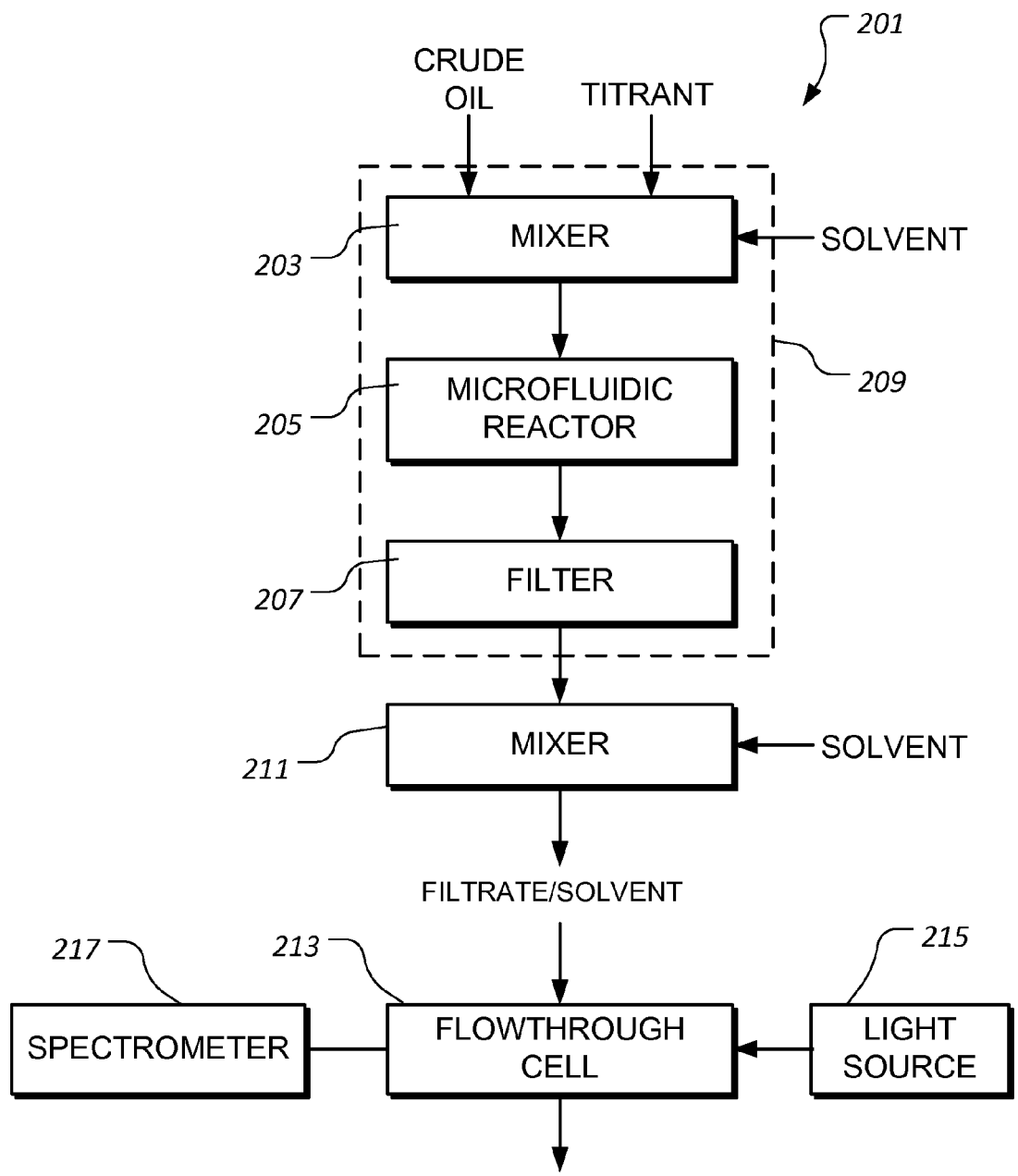
FIG. 2 is a graphical representation of an illustrative embodiment of a system for determining an asphaltene yield curve and an asphaltene flocculation point of a crude oil sample.

FIG. 2 is a graphical representation of a system 201 for determining an asphaltene yield curve and an asphaltene flocculation point of a crude oil sample. In the illustrated embodiment, a first mixer 203, for example a microfluidic mixer, is in fluid communication with a microfluidic reactor 205. Microfluidic reactor 205 is operably associated with a filter 207, for example, a membrane filter. Crude oil and a titrant, such as an alkane, like n-heptane, n-pentane, or such alkanes, are introduced into first mixer 203 wherein the crude oil and the titrant are mixed. The mixture is communicated into microfluidic reactor 205, wherein at least a portion of the asphaltene fraction is precipitated from the crude oil by the titrant, such that the asphaltene precipitate is dispersed in the remaining fraction. The maltene/precipitated asphaltene mixture is communicated to filter 207, which filters out the asphaltene precipitate, allowing a filtrate, comprising maltenes, unprecipitated asphaltenes, and, in some circumstances, excess titrant and solvent, to pass therethrough. First mixer 203, microfluidic reactor 205, and filter 207 may be operatively associated to form a microfluidic chip 209. System 201 further comprises a second mixer 211, which is in fluid communication with filter 207 and a flowthrough cell 213. The flowthrough cell 213 is operably associated with a light source 215 and a spectrometer 217 or other such device for determining an optical density of a fluid. As discussed with regard to FIG. 1, at times the filtrate expelled from filter 207 exhibits an optical density that is not within the measurement capabilities of spectrometer 217, or the filtrate may be more concentrated than the crude oil/solvent mixture. In such situations, a solvent, such as toluene, is introduced into mixer 211 along with the filtrate, to dilute the filtrate. The filtrate, along with any solvent added at mixer 211, is communicated to flowthrough cell 213, wherein the optical density of the filtrate/solvent mixture is determined by spectrometer 217.

In one embodiment, system 201 of FIG. 2 is configured such that, a solvent, such as toluene, can be selectively introduced into mixer 203 to aid in moving the crude oil through system 201, as well as to decrease the optical density of the crude oil sample for the purpose of determining the optical density of the crude oil. The crude oil and the solvent are communicated though mixer 203, microfluidic reactor 205, and filter 207 to flowthrough cell 213, wherein the optical density of the crude oil is determined by spectrometer 217.

Figure 3:
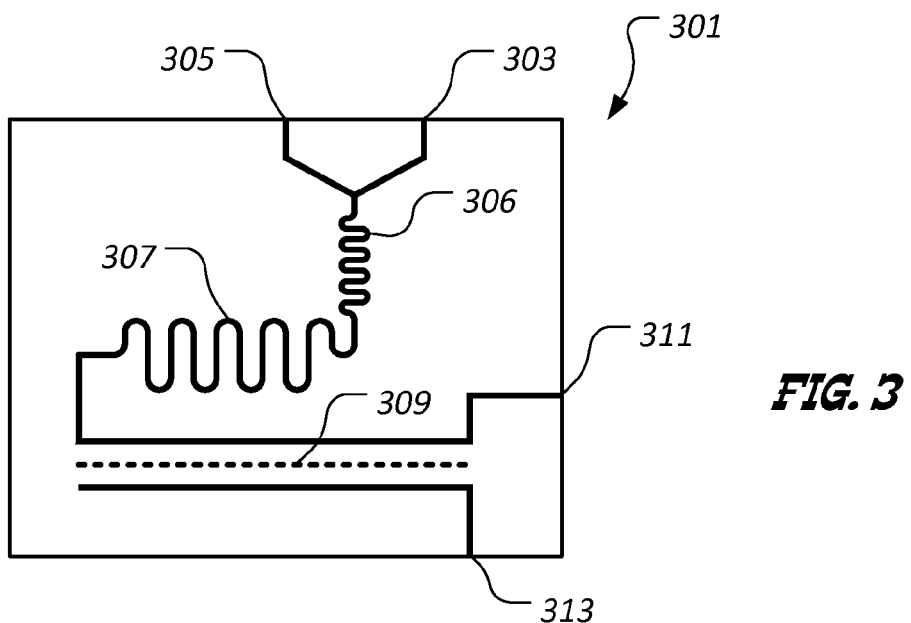
FIG. 3 is a schematic representation of a first illustrative embodiment of a microfluidic chip.

FIG. 3 depicts a schematic representation of an illustrative embodiment of a microfluidic chip 301, such as microfluidic chip 209, shown in FIG. 2. In the illustrated embodiment, microfluidic chip 301 includes a crude oil sample inlet port 303 and a solvent port 305. Solvent port 305 can be used to introduce a solvent, such as toluene, or a titrant or alkane, such as n-heptane or n-pentane, to microfluidic chip 301 depending upon the particular operation of microfluidic chip 301. Each of sample inlet port 303 and solvent port 305 are in fluid communication with a mixer section 306 and a reactor section 307, which comprises one or more serpentine channels. In the mixer section 306, the sample and the fluid introduced via solvent port 305 are mixed. In the reactor section 307, at least a portion of the asphaltene in the sample precipitates as asphaltene flocculate disposed in maltenes when the crude oil sample is mixed with an alkane. Microfluidic chip 301 further comprises a filter 309, such as a membrane filter, which is in fluid communication with reactor section 307. Filter 309 is configured to allow the maltenes, unprecipitated asphaltenes, and other such materials to pass therethrough but not to allow the asphaltene flocculate to pass therethrough. The asphaltene flocculate can be flushed from microfluidic chip 301 via a waste port 311 using a solvent introduced via solvent port 305. The maltenes, unprecipitated asphaltenes, and residual alkane or solvent are collected from microfluidic chip 301 via a product port 313.

Figure 4:
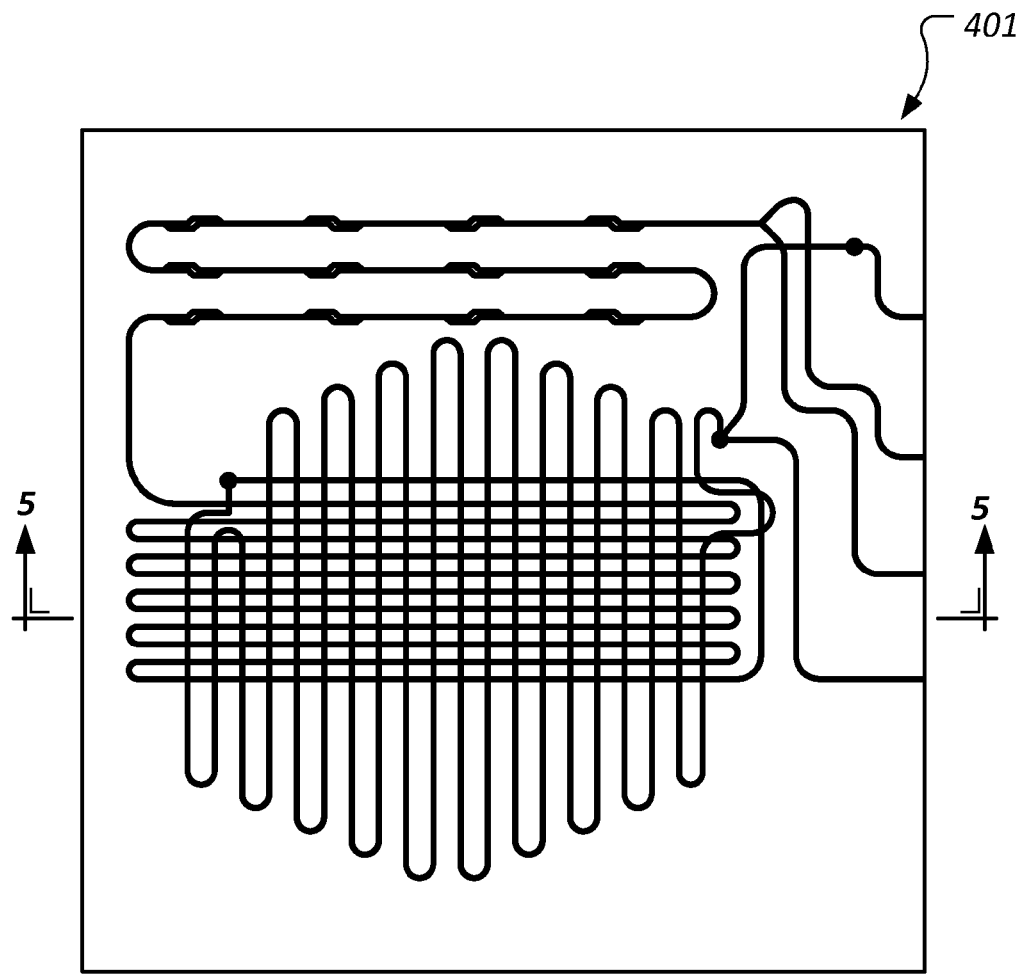
FIG. 4 is a top, plan view of a second illustrative embodiment of a microfluidic chip.
Figure 5:
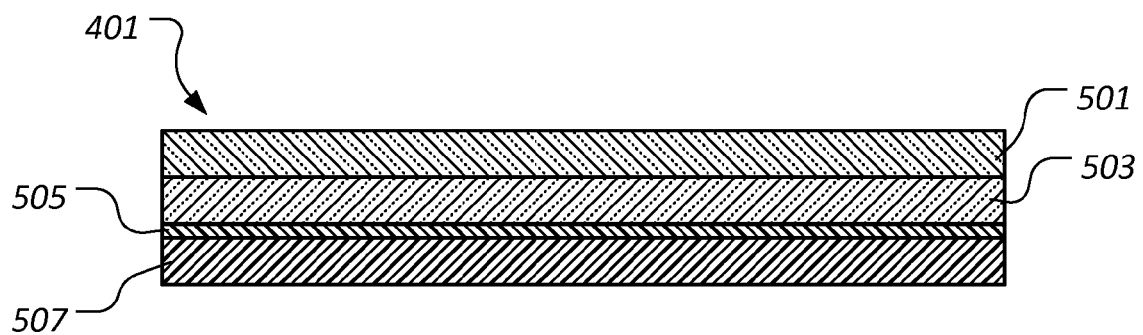
FIG. 5 is a sectional, elevational view of the microfluidic chip of FIG. 4.
Figure 6:
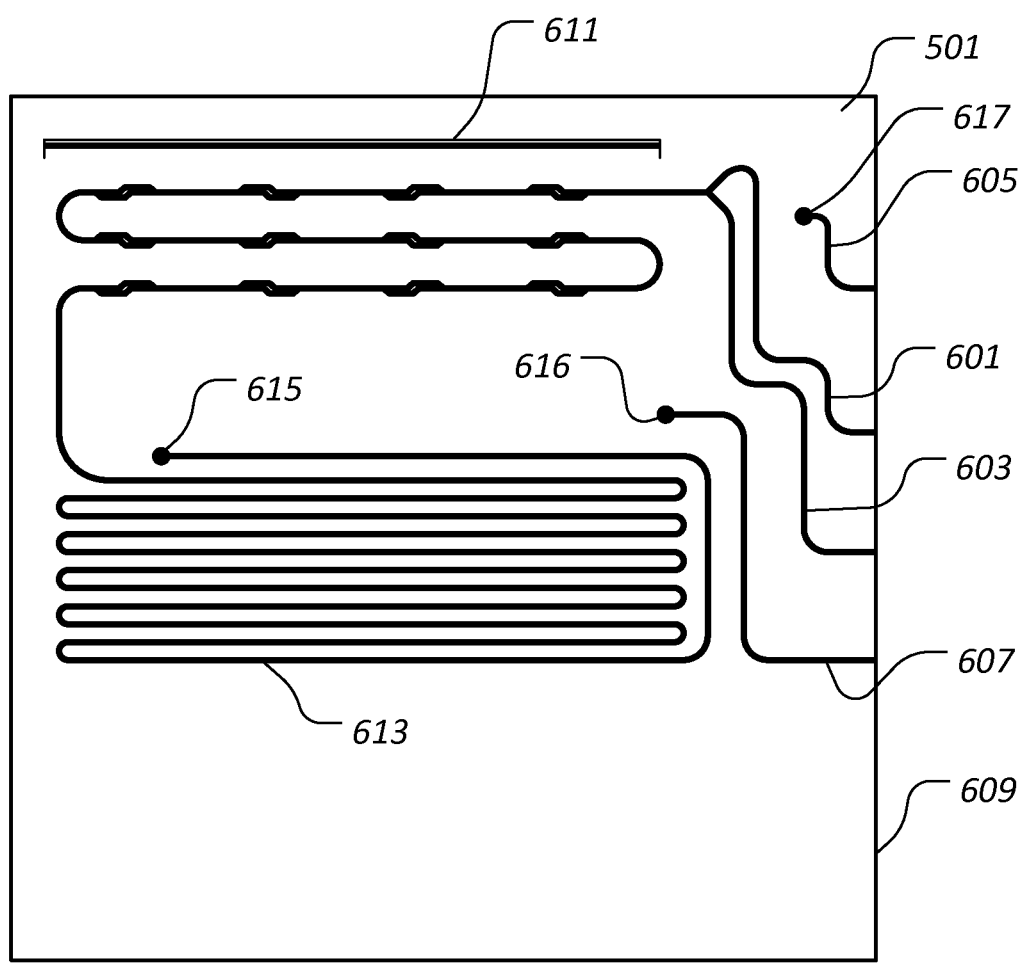
FIG. 6 is a top, plan view of an upper portion of the microfluidic chip of FIG. 4.
Figure 7:
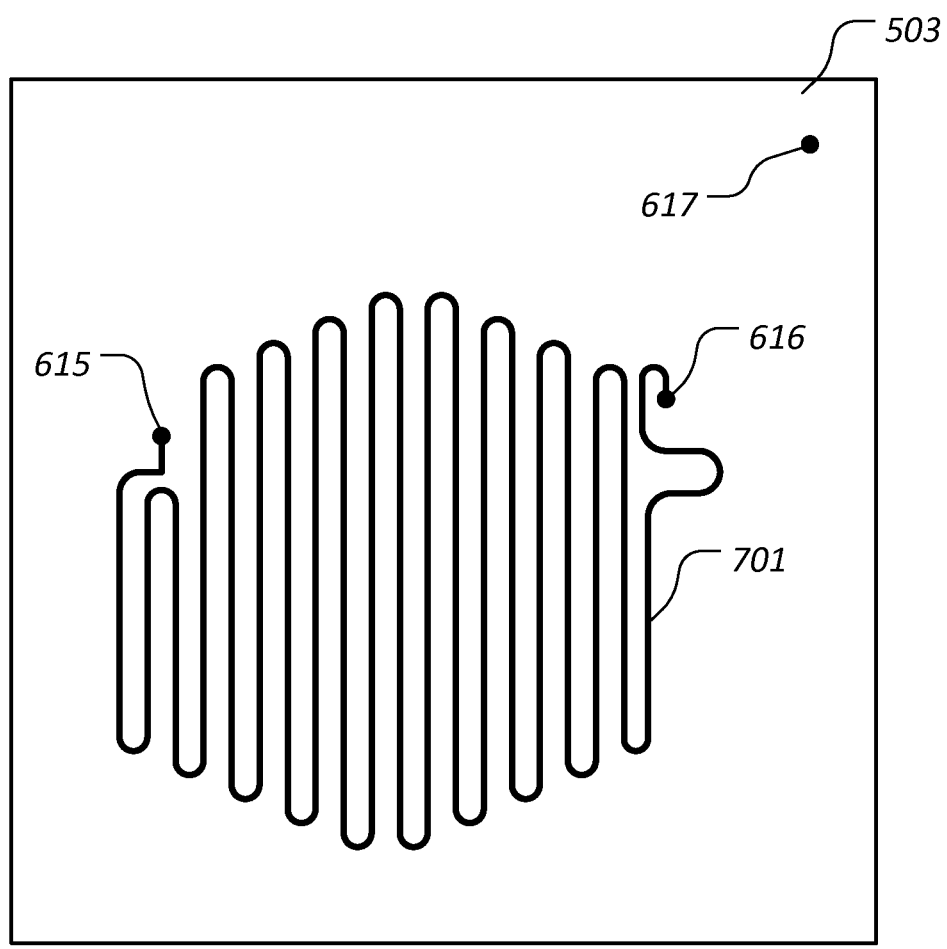
FIG. 7 is a top, plan view of an intermediate portion of the microfluidic chip of FIG. 4.
Figure 8:
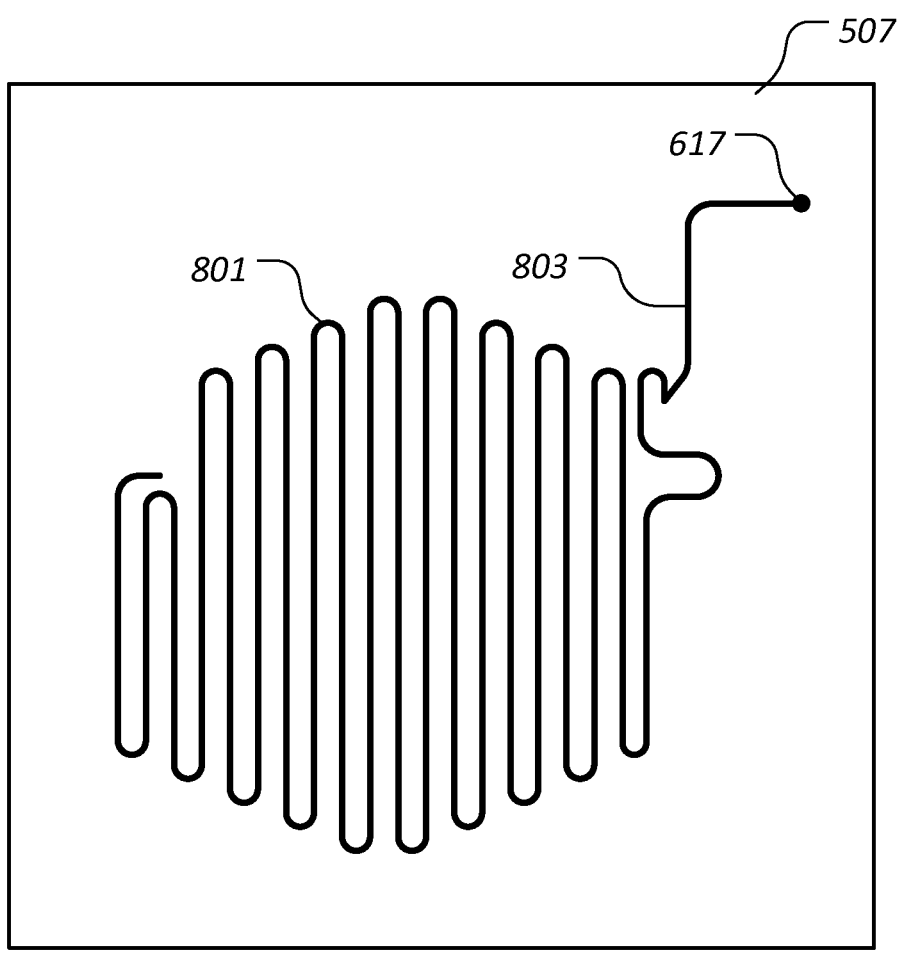
FIG. 8 is a top, plan view of a lower portion of the microfluidic chip of FIG. 4.

FIGS. 4-8 depict a microfluidic chip 401, which is a particular implementation of microfluidic chip 301 of FIG. 3. FIG. 4 is a top, plan view of microfluidic chip 401, while FIG. 5 is a sectional, elevational view of microfluidic chip 401. As can be seen in FIG. 5, microfluidic chip 401 comprises an upper portion 501, an intermediate portion 503, a filtration membrane 505, and a lower portion 507. Filtration membrane 505 is disposed between intermediate portion 503 and lower portion 507. Each of portions 501, 503, and 507 define certain channels for transporting crude oil and/or other fluids through microfluidic chip 401. Crude oil and solvent are introduced into upper portion 501 of microfluidic chip 401, wherein the crude oil and solvent are mixed to induce separation of asphaltenes from the crude oil. The asphaltene flocculate is filtered from the mixture by filtration membrane 505, allowing the maltenes and the remaining titrant or solvent to pass therethrough into lower portion 507. The maltenes and any remaining titrant or solvent are then routed from microfluidic chip 401 via lower portion 507 and upper portion 501. To better illustrate the particular aspects of microfluidic chip 401, FIG. 6 depicts channels defined only in upper portion 501, FIG. 7 depicts channels defined only in intermediate portion 503, and FIG. 8 depicts channels defined only in lower portion 507.

Referring now to FIG. 6, upper portion 501 of microfluidic chip 401 defines a sample inlet port 601, a solvent port 603, a product port 605, and a waste port 607. It should be noted that a solvent or a titrant, such as an alkane, may be introduced into microfluidic chip 401 via solvent port 603 depending upon the particular operation of microfluidic chip 401. Sample inlet port 601 and solvent port 603 are channels defined by upper portion 501 that lead from an edge 609 of upper portion 501 to a mixing channel 611 defined by upper portion 501. In the illustrated embodiment, mixing channel 611 is a microfluidic mixing channel, although other types of mixing devices are contemplated. Mixing channel 611 is in fluid communication with a first serpentine channel 613 (reactor), which routes fluids through upper portion 501 of microfluidic chip 401 to a transfer port 615, which is in fluid communication with a second serpentine channel 701 (FIG. 7) defined by intermediate portion 503.

Referring now to FIG. 7, intermediate portion 503 of microfluidic chip 401 defines a second serpentine channel 701, which routes fluids through intermediate portion 503 of microfluidic chip 401. First serpentine channel 613, shown in FIG. 6, defines a microfluidic reactor of microfluidic chip 401, while the length and width of second serpentine channel 701 determines the amount of asphaltenes that can be stored in microfluidic chip 401, and hence the amount of fluid that can be processed in one cycle. Within the microfluidic reactor, that is, within first serpentine channel 613, titrant introduced via solvent port 603 induces precipitation of asphaltenes. The microfluidic reactor is sufficient in length to allow adequate time for asphaltene flocculate growth within the microfluidic reactor. Second serpentine channel 701 is in fluid communication generally entirely with filtration membrane 505, shown in FIG. 5. Thus, fluids flowing through second serpentine channel 701 are filtered by filtration membrane 505, such that fluids are allowed to pass through filtration membrane 505. However, particulates, such as asphaltene flocculate, are substantially retained by filtration membrane 505 and not allowed to pass therethrough. Second serpentine channel 701 is also connected to waste port 607 by transfer port 616.

Referring now to FIGS. 6 and 8, the filtrate is collected in a filter channel 801, and then routed via a product channel 803, each defined by lower portion 507. In the illustrated embodiment, filter channel 801 exhibits substantially the same shape as second serpentine channel 701 of intermediate portion 503, shown in FIG. 7. Product channel 803 is in fluid communication with product port 605 via a transfer port 617. Transfer port 617 and product port 605 are each defined by upper portion 501. The filtered fluid is subsequently inspected, such as by using optical spectroscopy, to determine the optical density of the filtered fluid. Referring in particular to FIG. 6, waste, that is, the materials that do not pass through filtration membrane 505, are routed or flushed to waste port 607.

Referring in particular to FIG. 5, in one embodiment, upper portion 501 and intermediate portion 503 may comprise B 270® glass, available from SCHOTT North America, Inc. of Elmsford, N.Y., USA, fused silica, or the like. In one embodiment, upper portion 501 is generally about one millimeter thick and intermediate portion 503 is generally about two millimeters thick. Channels, ports, and the like defined by upper portion 501 and/or intermediate portion 503 are, in one embodiment, etched isotropically into the portions using, for example, a wet etching process. In one embodiment, one, some, or all of the channels, ports, and the like defined by upper portion 501 and intermediate portion 503 exhibit a plurality of depths, ranging from about 50 micrometers to about 250 micrometers and are produced using a multi-phase masking process. In one embodiment, lower portion 507 comprises polyetheretherketone (PEEK). In one embodiment, components of microfluidic chip 401 are mounted in a chip holder to locate the components relative to one another. In one embodiment, the chip holder includes a case housing highly-sprung bolts arranged about microfluidic chip 401. In a certain embodiment, when the bolts reach a "dead-stop", the clamp provides a compression force of about 600 Newtons to create a partial seal over filtration membrane 505. Thus, fluid passing through filtration membrane 505 is collected downstream of membrane 505 in the chip holder and guided to the output for analysis, while precipitated asphaltene flocculate is held back and collects on the filtration membrane 505. In one embodiment, filtration membrane 505 comprises a polytetrafluoroethylene (PTFE) membrane with an average pore size of about 200 nm; however, membranes made of other materials and with different pore sizes are also contemplated.

Figure 9:
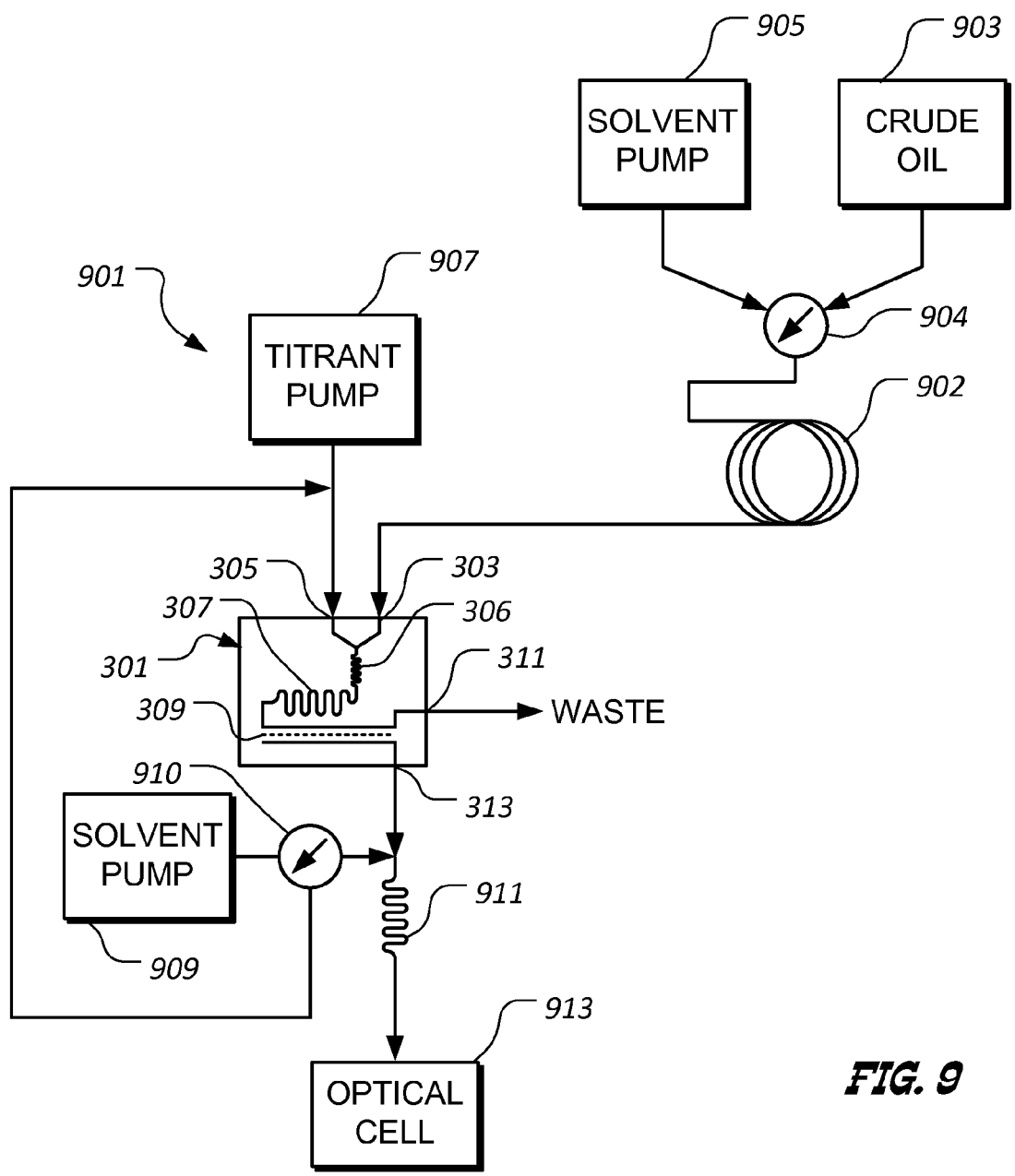
FIG. 9 is a schematic representation of an illustrative embodiment of a system for determining an asphaltene yield curve and an asphaltene flocculation point of a crude oil sample.

FIG. 9 depicts a particular, illustrative embodiment of a system 901 for determining the degree of asphaltene precipitation from a crude oil sample based upon titrant concentration. System 901 is depicted as comprising microfluidic chip 301, shown in FIG. 3; however, system 901 may comprise microfluidic chip 401, shown in FIGS. 4-8, or any other configuration contemplated by the disclosure or its equivalent. In the illustrated embodiment, system 901 comprises a sample loop 902 in which a sample of crude oil is disposed after having been injected therein by, for example, a syringe pump, from crude oil sample reservoir 903 through a first switching valve 904. Sample loop 902 is in fluid communication with a first solvent pump 905, via first switching valve 904, and sample inlet port 303 of microfluidic chip 301. System 901 further comprises a titrant pump 907, which is in fluid communication with solvent port 305 of microfluidic chip 301. System 901 further comprises a second solvent pump 909 in fluid communication with solvent port 305 and product port 313 through a second switching valve 910, and a mixer 911 in fluid communication with second solvent pump 909, product port 313, and an optical cell 913, which may include a spectrometer. In one embodiment, first solvent pump 905, second solvent pump 909, and titrant pump 907 are syringe pumps.

In a first particular operation of system 901, crude oil from crude oil sample reservoir 903 is first injected into sample loop 902 through first switching valve 904. Thereafter, the alignment of first switching valve 904 is switched and a solvent, such as toluene, is urged into sample loop 902 by first solvent pump 905 to urge the crude oil sample disposed therein into sample inlet port 303 of microfluidic chip 301. The oil sample passes through filter 309 substantially in its entirety. In one embodiment, system 901 operates first solvent pump 905 and second solvent pump 909 to introduce the solvent into microfluidic chip 301 at a mixing ratio to dilute the crude oil sample sufficiently so that optical cell 913 can determine the optical density of the diluted crude oil. In this way, the same system 901 can be used to both determine the optical density of crude oil and the maltene component of crude oil. Second solvent pump 909 may also be used to introduce solvent directly into solvent port 305.

In a second particular operation of system 901, a solvent, such as toluene, is urged into sample loop 902 by first solvent pump 905 to urge the crude oil sample disposed therein into sample inlet port 303 of microfluidic chip 301. Titrant pump 907 then urges a titrant, such as an alkane like n-heptane, into solvent port 305 of microfluidic chip 301. In one embodiment, system 901 operates first solvent pump 905 and titrant pump 907 to introduce the alkane into microfluidic chip 301 at a predetermined mixing ratio, such as 40 parts alkane to one part crude oil. The alkane and crude oil are mixed and the resulting flocculated asphaltenes are filtered, leaving maltenes, unprecipitated asphaltenes, and residual alkane material, as described herein regarding microfluidic chips 301 and 401. If the concentration of the filtrate exiting product port 313 of microfluidic chip 301 is inappropriately high, second solvent pump 909 introduces solvent to mixer 911, so that the filtrate is diluted. The maltenes, unprecipitated asphaltenes, and residual alkane material, that is, the filtrate or diluted filtrate, are then routed to optical cell 913 to determine their optical density.

Figure 10:
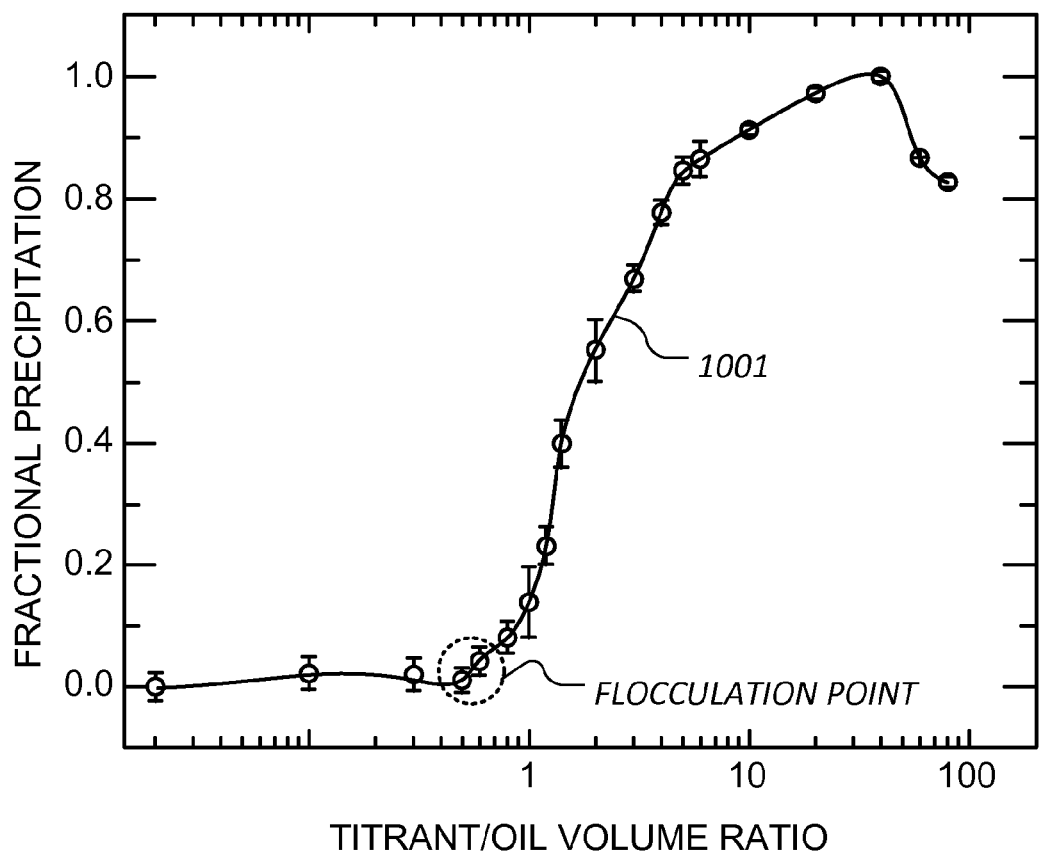
FIG. 10 is a graphical representation of an asphaltene yield curve and an asphaltene flocculation point for a particular crude oil sample.

FIG. 10 depicts a first asphaltene yield curve 1001 generally at room temperature for a particular crude oil sample, representing the relationship of the fractional precipitation of asphaltenes of the crude oil sample to the titrant/oil volume ratio. In this case, the titrant is n-heptane. As expected, the fractional asphaltene precipitation is virtually zero at low titrant concentrations. At a titrant/crude oil volume ratio of about 0.6:1, the first asphaltenes are precipitated. This concentration is considered to be the asphaltene flocculation point. As the concentration of titrant increases, so does the amount of flocculated or precipitated asphaltenes. The asphaltene yield achieves a maximum at about 40:1 in this example. At ratios higher than about 40:1, the amount of asphaltene precipitated decreases markedly, due to an increase in solubility of asphaltenes at infinite dilutions.

Figure 11:
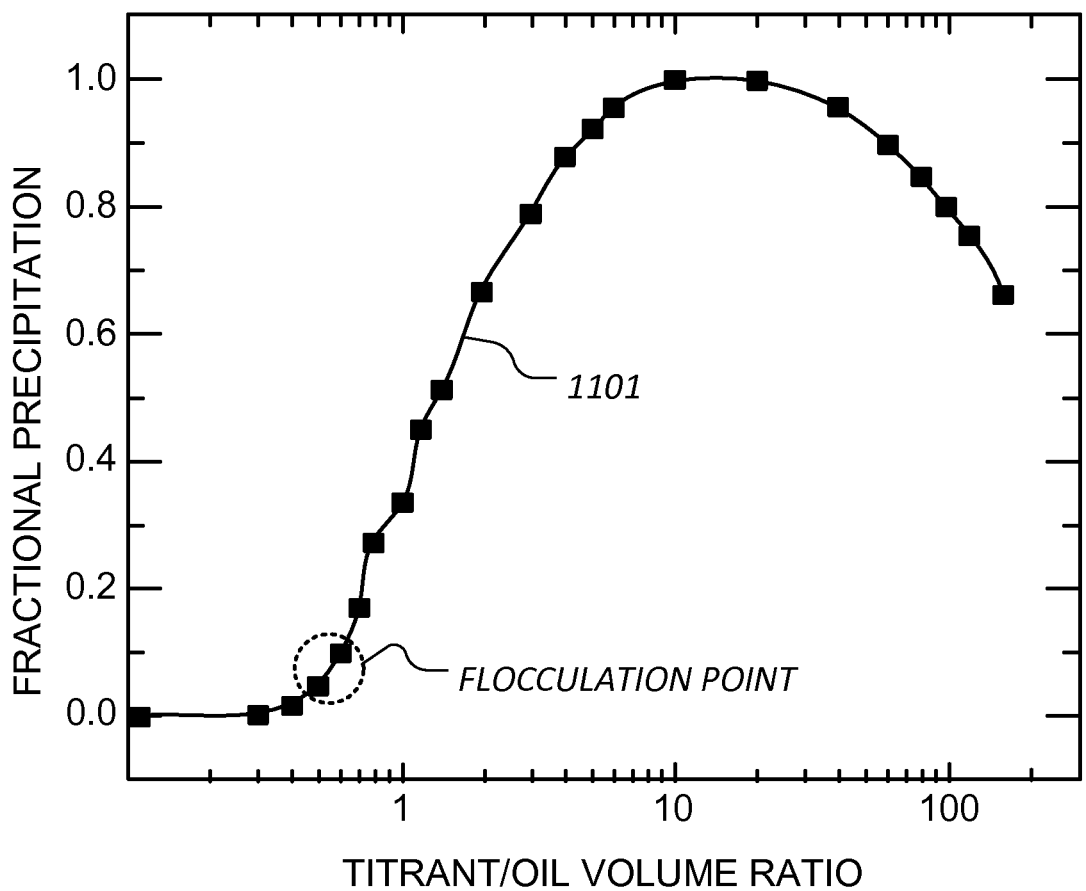
FIG. 11 is a graphical representation of an asphaltene yield curve and an asphaltene flocculation point for a particular crude oil sample.

FIG. 11 depicts a second asphaltene yield curve 1101 at a temperature of about 65 degrees Celcius for another, particular crude oil sample. Similar to the example shown in FIG. 10, the yield curve 1101 depicts little or no asphaltene precipitation at low titrant volume ratios. The asphaltene flocculation point in this example is at a titrant/crude oil volume ratio of about 0.4:1. The maximum precipitation occurs at a titrant/crude oil ratio of about 10:1. Beyond this ratio, a substantial decrease in asphaltene precipitation is observed. Using the disclosed subject matter of the application, 23 experiments were performed to acquire the data for yield curve 1101.

Figure 12:
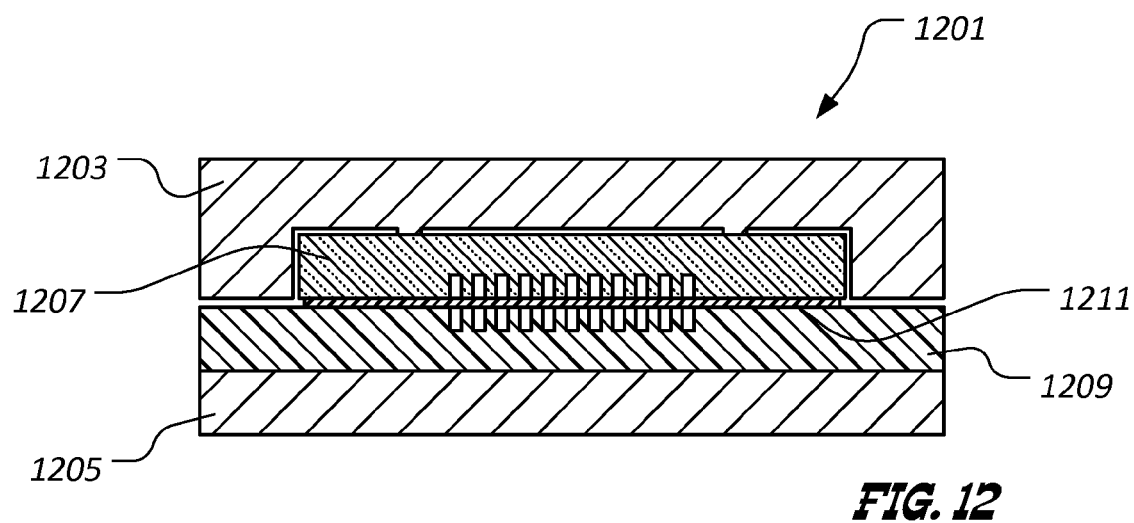
FIGS. 12 and 13 are stylized, cross-sectional views of illustrative embodiments of microfluidic chip assemblies.
Figure 13:
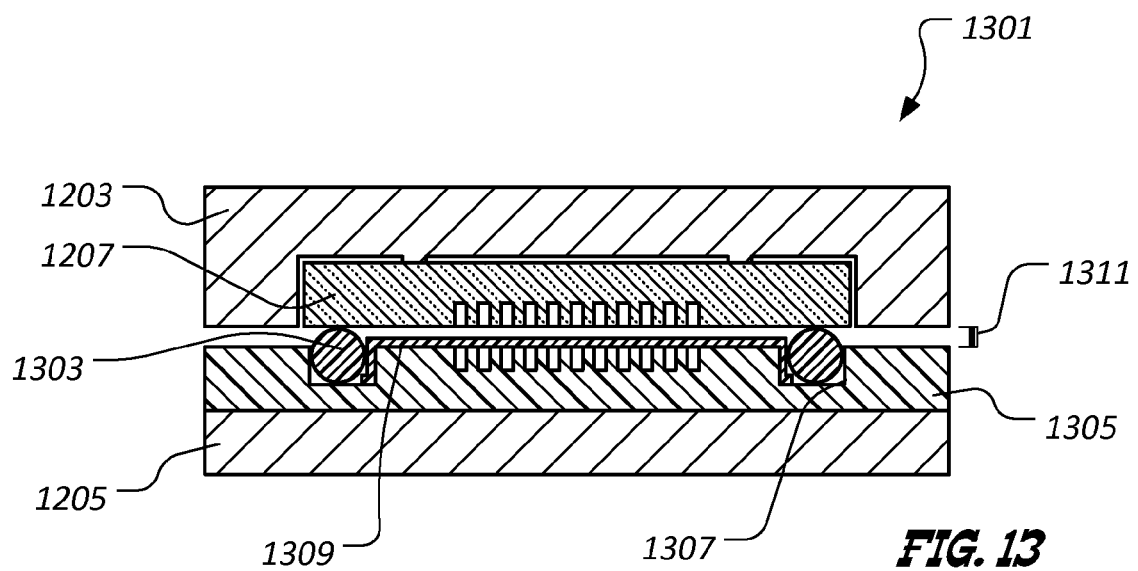

FIGS. 12 and 13 illustrate microfluidic chip assemblies 1201 and 1301, respectively, which include embodiments of microfluidic chips, such as microfluidic chip 401 of FIG. 4, and further include an upper clamp 1203 and a lower clamp 1205 for at least retaining other elements of the microfluidic chip assemblies. Referring to FIG. 12, microfluidic chip assembly 1201 further includes an upper portion 1207 and a lower portion 1209, with a membrane filter 1211 disposed therebetween, such that lower portion 1209 is in fluid communication with upper portion 1207 via membrane filter 1211. In some implementations, leakage can occur between membrane filter 1211 and upper portion 1207 and/or between membrane filter 1211 and lower portion 1209. Accordingly, the disclosed subject matter of the application further includes the microfluidic chip assembly 1301, shown in FIG. 13, further comprising a seal 1303, such as an O-ring or the like, disposed between and providing sealing engagement between upper portion 1207 and an alternative lower portion 1305. Lower portion 1305 defines a seat or groove 1307 in which seal 1303 is disposed and into which a membrane filter 1309 extends. Seal 1303, in some embodiments, also spaces upper portion 1207 away from lower portion 1305, which provides a gap 1311. Gap 1311 provides a volume in which flocculated asphaltenes can accumulate, thus allowing longer run times at low titrant/oil mixing ratios.

Figure 14:
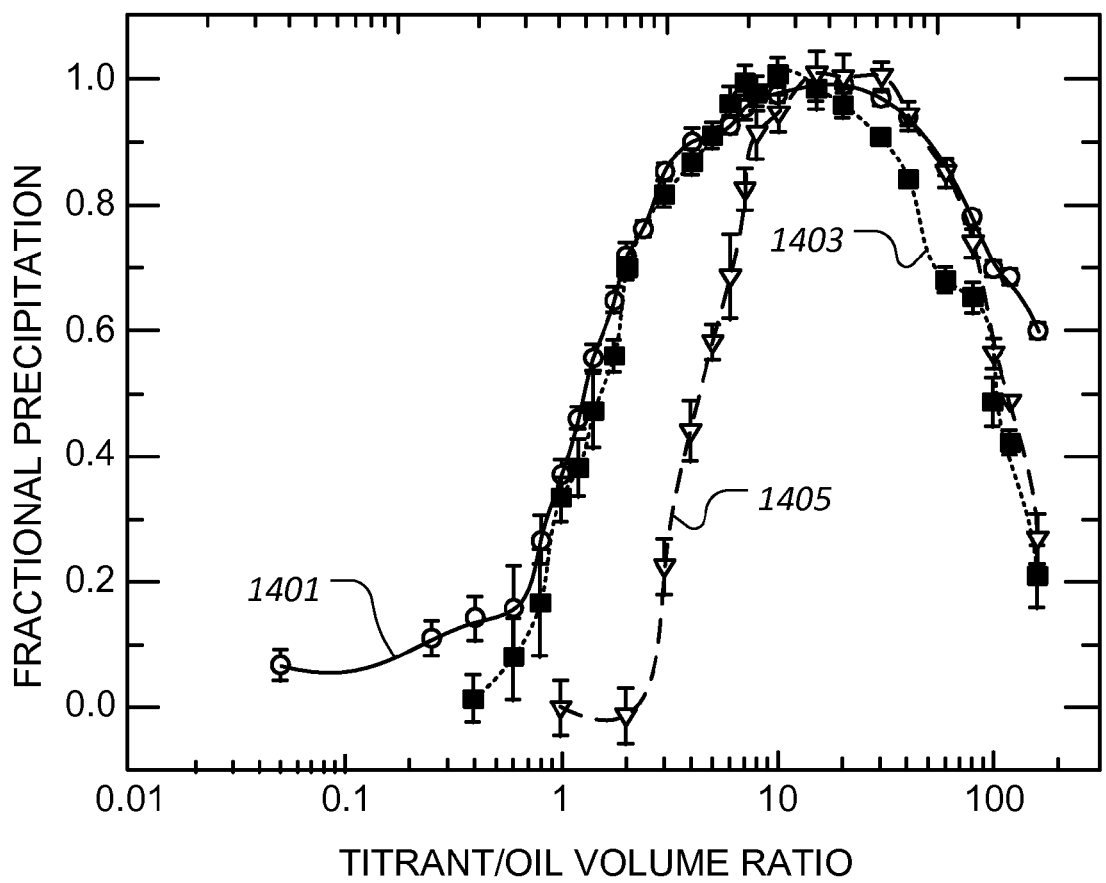
FIG. 14 is a graphical representation of asphaltene yield curves for different crude oil samples.

FIG. 14 is a graphical representation of yield curves 1401, 1403, and 1405 for three different crude oil samples derived from data taken at about 25 degrees Celcius using the methodology of the disclosed subject matter of the application. Note that different flocculation points, maxima, and yield curve shapes are exhibited for each different crude oil sample.

Figure 15:
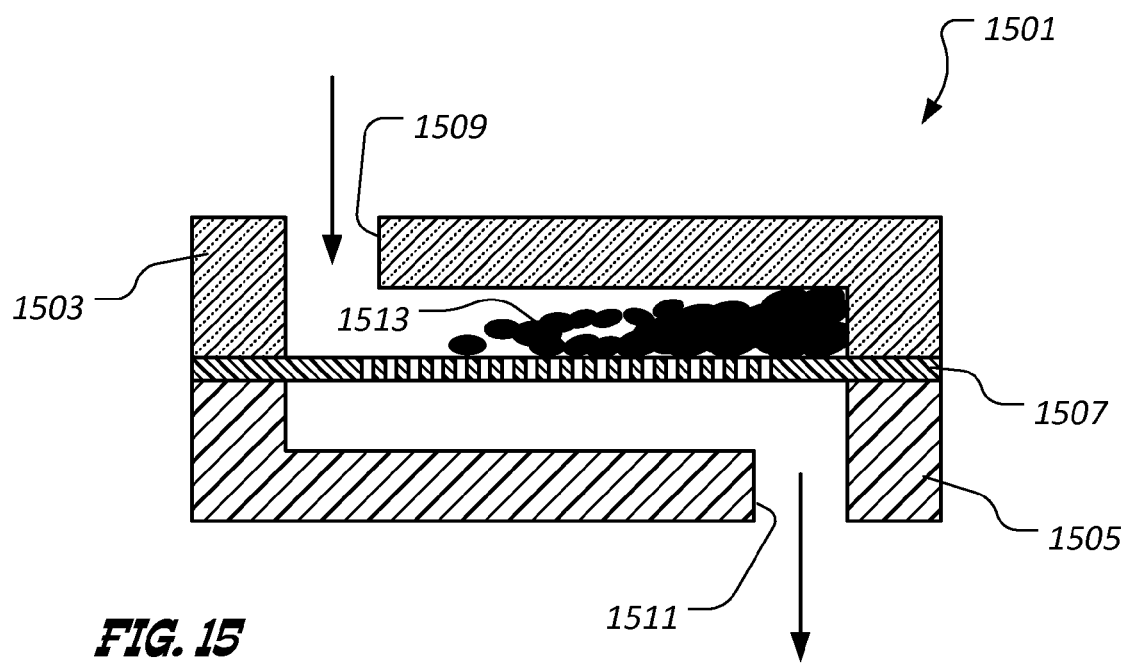
FIGS. 15 and 16 are stylized, cross-sectional views of illustrative embodiments of a microfluidic chip.
Figure 16:
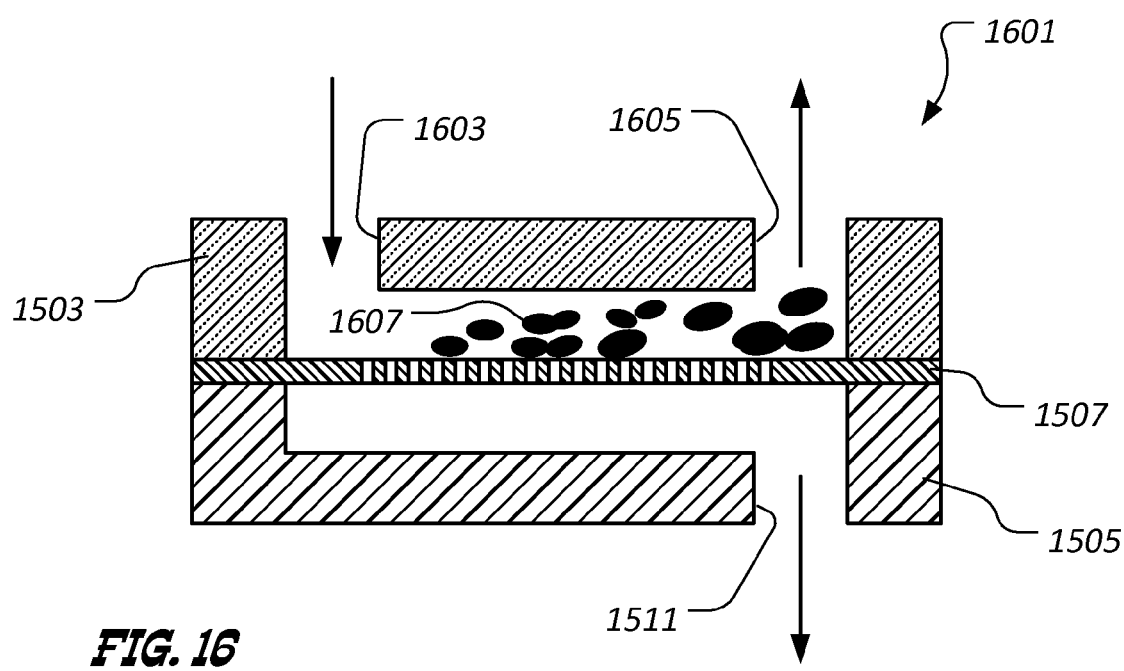

FIGS. 15 and 16 provide further embodiments of microfluidic chips 1501 and 1601, respectively, such as microfluidic chip 401 of FIG. 4. In microfluidic chip 1501, an upper portion 1503 and a lower portion 1505 are provided, along with a membrane filter 1507 disposed therebetween. Upper portion 1503 defines an inlet 1509, through which the titrant/oil mixture is inputted to microfluidic chip 1501, and lower portion 1505 defines an outlet 1511, through which filtered fluid is outputted from microfluidic chip 1501. In some implementations, excessive asphaltene flocculate 1513 can build up on membrane filter 1507, causing clogging and shortening run times. Accordingly, the disclosed subject matter of the application further includes an embodiment corresponding to microfluidic chip 1601, which generally corresponds to microfluidic chip 1501 except that upper portion 1503 defines both an inlet 1603 and an outlet 1605. Outlet 1605 allows filtered asphaltene flocculate to be removed from microfluidic chip 1601 along with the retentant flow, resulting in a reduced mass of asphaltene flocculate 1607 disposed at membrane filter 1507.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. A method for determining an asphaltene yield curve and an asphaltene flocculation point, comprising:
   a. obtaining a crude oil sample;
   b. measuring an optical spectrum of the crude oil sample;
   c. setting a minimum titrant concentration;
   d. mixing the crude oil sample with a titrant to produce a crude oil-titrant mixture;
   e. filtering precipitated asphaltenes, if any, from the crude oil-titrant mixture to produce a filtrate;
   f. measuring an optical spectrum of the filtrate; and
   g. subtracting the optical spectrum of the filtrate from the optical spectrum of the crude oil sample;
   h. wherein the titrant concentration is increased and steps d-g are repeated until a predetermined maximum titrant concentration is reached; and
   further comprising:
   i. determining a fractional asphaltene precipitation for each concentration of titrant from the optical spectrum resulting from step g; and
   j. determining a flocculation point corresponding to an inflection point in the fractional asphaltene precipitation data generated in step i.

2. The method of claim 1, further comprising adding a solvent to the filtrate before measuring the optical spectrum of the filtrate.

3. The method of claim 2, wherein the solvent is toluene.

4. The method of claim 1, further comprising adding a solvent to the crude oil sample before measuring the optical spectrum of the crude oil sample.

5. The method of claim 4, wherein the solvent is toluene.

6. The method of claim 1, wherein the titrant is an alkane.

7. The method of claim 6, wherein the alkane is n-heptane or n-pentane.

8. A system for determining an asphaltene yield curve and an asphaltene flocculation point, comprising:
   a first mixer in fluid communication with a crude oil source and a titrant source;
   a microfluidic reactor in fluid communication with the first mixer;
   a filter in fluid communication with the microfluidic reactor;
   a second mixer in fluid communication with the filter and in fluid communication with a solvent source; and
   an optical cell operably associated with the second mixer.

9. The system of claim 8, wherein the first mixer is in fluid communication with a solvent source.

10. The system of claim 8, wherein the solvent source is a solvent pump.

11. The system of claim 8, wherein the first mixer, the microfluidic reactor, and the filter comprise a microfluidic chip.

12. The system of claim 11, wherein the microfluidic chip comprises:
    an upper portion;
    a lower portion; and
    a membrane filter disposed between the upper portion and the lower portion.

13. The system of claim 12, wherein the lower portion defines a seat and the microfluidic chip further comprises a seal, sealingly engaged with the upper portion and the seat.

14. The system of claim 13, wherein the seal spaces the upper portion away from the lower portion.

15. The system of claim 12, wherein the upper portion defines an inlet and an outlet, such that accumulated asphaltene flocculate can be removed from the microfluidic chip via the outlet.

16. The system of claim 8, wherein at least one of the first mixer and the second mixer is a microfluidic mixer.

17. The system of claim 8, wherein the crude oil source is disposed in a sample loop.

18. The system of claim 8, further comprising a solvent source for urging the crude oil sample to the first mixer.

19. The system of claim 8, wherein the filter is a membrane filter.

20. The system of claim 8, wherein the optical cell is operably associated with a spectrometer.

21. A system for determining an asphaltene yield curve and an asphaltene flocculation point, comprising:
    a microfluidic chip;
    a mixer operably associated with the microfluidic chip;
    a first solvent pump in fluid communication with the mixer; and
    an optical cell;
    wherein the microfluidic chip comprises:
    a crude oil sample inlet port;
    a titrant port;
    a mixer section in fluid communication with the crude oil sample inlet port and the titrant port;
    a reactor section in fluid communication with the mixer section;
    a filter in fluid communication with the reactor section, the filter having an inlet side and an outlet side;
    a waste port in fluid communication with the inlet side of the filter, and;
    a product port in fluid communication with the outlet side of the filter and with the optical cell.

22. The system of claim 21, further comprising:
- a second solvent pump; and
- a sample loop in fluid communication with the second solvent pump and the crude oil sample inlet port.

23. The system of claim 21, further comprising a titrant pump in fluid communication with the titrant port.

24. The system of claim 21, wherein the optical cell is operably associated with a spectrometer.

* * * * *